US012650297B2

(12) United States Patent
Van Dusschoten et al.

(10) Patent No.: US 12,650,297 B2
(45) Date of Patent: Jun. 9, 2026

(54) METHOD OF AND SYSTEM FOR REPRESENTING SHAPE OF AN OPTICAL FIBER SENSOR

(71) Applicant: KONINKLIJKE PHILIPS N.V., Eindhoven (NL)

(72) Inventors: Anna Hendrika Van Dusschoten, Eindhoven (NL); Jeroen Jan Lambertus Horikx, Weert (NL); Gert Wim 'T Hooft, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 488 days.

(21) Appl. No.: 18/025,857

(22) PCT Filed: Sep. 8, 2021

(86) PCT No.: PCT/EP2021/074637
§ 371 (c)(1),
(2) Date: Mar. 10, 2023

(87) PCT Pub. No.: WO2022/058207
PCT Pub. Date: Mar. 24, 2022

(65) Prior Publication Data
US 2023/0417542 A1 Dec. 28, 2023

(30) Foreign Application Priority Data
Sep. 16, 2020 (EP) .................................... 20196405

(51) Int. Cl.
G01B 11/16 (2006.01)
A61B 34/20 (2016.01)

(52) U.S. Cl.
CPC ............ *G01B 11/18* (2013.01); *G01B 11/161* (2013.01); *A61B 34/20* (2016.02); *A61B 2034/2061* (2016.02)

(58) Field of Classification Search
CPC ....... G01B 11/18; G01B 11/161; A61B 34/20; A61B 2034/2061
(Continued)

(56) References Cited

U.S. PATENT DOCUMENTS 7,324,714 B1 * 1/2008 Cranch .................. G01B 11/18
250/227.16
8,773,650 B2 * 7/2014 Froggatt ................ G01B 11/18
356/73.1
(Continued)

FOREIGN PATENT DOCUMENTS

CN 105658268 A * 6/2016 ........ A61M 25/0158
EP 3627096 A1 3/2020
(Continued)

OTHER PUBLICATIONS

International Search report and Written Opinion of PCT/EP2021/074637 dated Nov. 29, 2021.

*Primary Examiner* — Peter J Macchiarolo
*Assistant Examiner* — Monica S Young

(57) ABSTRACT

The present invention relates to a method of representing shape of an optical fiber sensor (12) having a central core (16) and a plurality of outer cores (14, 18, 20), each core comprising one or more sensing elements, the method comprising: (a) optically interrogating the cores (14, 16, 18, 20) of the fiber sensor (12) from an incident optical wave over a wavelength range centered on a resonance wavelength of the one or more sensing elements, wherein the wavelength range is associated with a detection limited to a minimum radius of curvature along the fiber sensor; (b) reconstructing the shape of the fiber sensor (12) involving processing of interferometric signals received from the optical interrogation of the cores (14, 16, 18, 20), including reconstructing the shape of at least one out-of-range section along the fiber sensor (12) which is a section having a radius (Continued)

of curvature lower than the minimum radius of curvature, wherein reconstructing the shape of the at least one out-of-range section includes calculating curvature of the fiber sensor (12) in the at least one out-of-range section from interferometric signals received from the interrogation of the central core (16) in the at least one out-of-range section; (c) displaying the shape of the fiber sensor (12) including the at least one out-of-range section. A system to carry out the method is also described.

15 Claims, 5 Drawing Sheets

(58) Field of Classification Search
USPC .......................................................... 73/800
See application file for complete search history.

(56) References Cited

U.S. PATENT DOCUMENTS

| | | | |
|---|---|---|---|
| 9,784,569 | B2 | 10/2017 | Froggatt et al. |
| 10,586,081 | B2 * | 3/2020 | Austerlitz .......... G01D 5/35316 |
| 11,249,248 | B2 * | 2/2022 | Kashyap .............. G02B 6/4266 |
| 11,519,760 | B2 | 12/2022 | Van Dusschoten et al. |
| 2004/0083808 | A1 * | 5/2004 | Rambow ............ G01D 5/35303 |
| | | | 73/250 |

| | | | |
|---|---|---|---|
| 2007/0156019 | A1 * | 7/2007 | Larkin ................... A61B 34/30 |
| | | | 600/104 |
| 2007/0201793 | A1 * | 8/2007 | Askins ............... G02B 6/02042 |
| | | | 385/5 |
| 2010/0215311 | A1 * | 8/2010 | Moore ................... G01B 11/18 |
| | | | 356/73.1 |
| 2012/0197097 | A1 * | 8/2012 | Chan ...................... A61B 1/009 |
| | | | 600/478 |
| 2013/0345719 | A1 * | 12/2013 | Donhowe .......... A61B 1/00167 |
| | | | 385/13 |
| 2014/0053654 | A1 * | 2/2014 | Rogge .................... G01L 1/246 |
| | | | 73/800 |
| 2014/0240713 | A1 * | 8/2014 | Kemp ..................... G01L 1/246 |
| | | | 356/601 |
| 2019/0033062 | A1 * | 1/2019 | Horikx .............. G01M 11/3172 |
| 2019/0234727 | A1 * | 8/2019 | Roye ...................... A61B 34/35 |
| 2019/0250050 | A1 * | 8/2019 | Sanborn ................ G01B 11/18 |
| 2020/0264018 | A1 * | 8/2020 | Froggatt ........... G02B 6/02076 |
| 2020/0300614 | A1 * | 9/2020 | Van Putten ........... G01B 11/18 |
| 2022/0049950 | A1 | 2/2022 | Van Dusschoten et al. |

FOREIGN PATENT DOCUMENTS

| | | | | |
|---|---|---|---|---|
| JP | WO-2017085878 | A1 * | 9/2018 | ............. G01B 11/18 |
| WO | 2020058376 | A1 | 8/2016 | |
| WO | 2016122742 | A1 | 3/2020 | |

* cited by examiner

METHOD OF AND SYSTEM FOR REPRESENTING SHAPE OF AN OPTICAL FIBER SENSOR

CROSS-REFERENCE TO PRIOR APPLICATIONS

This application is the U.S. National Phase application under 35 U.S.C. § 371 of International Application No. PCT/EP2021/074637, filed on Sep. 8, 2021, which claims the benefit of European Patent Application No. 20196405.3 filed on Sep. 16, 2020. These applications are hereby incorporated by reference herein.

FIELD OF THE INVENTION

The present invention generally relates to methods of representing shape of an optical fiber sensor. More particularly, the invention relates to a method of representing shape of an optical fiber sensor having a central core and a plurality of outer cores, each core comprising one or more sensing elements. The invention further relates to a system for representing shape of an optical fiber sensor. Still further, the invention relates to a computer program suitable for causing the system to carry out the above-mentioned method.

BACKGROUND OF THE INVENTION

Optical shape sensing (OSS) is a technology with which the three-dimensional shape of a special optical fiber sensor can be reconstructed from the reflections of light within the fiber sensor. This technology enables, for example, real-time 3D visualization of the full shape of devices like medical devices, for example catheters and guidewires. The shapes of the medical devices can be overlaid on X-ray images or a pre-operative CT scan. In this way, a physician can navigate the devices during a procedure without the need of X-ray tracking.

In optical shape sensing, distributed strain and temperature signals are obtained from back-scattered spectra obtained with an interrogator system that incorporates interferometers. This is done for an optical fiber sensor with, for example, three outer cores helically wound around a fourth core, which is in the center of the fiber sensor. The responses of the cores to strain and temperature are measured as phase differences of the optical signals from the interferometer, as a function of position along the fiber sensor. The phase differences are obtained with respect to a reference measurement in which the fiber sensor lies in a well-defined shape, for example a completely straight shape. From the phase difference, the strain and temperature differences can be deduced for each core. The strain signals will be the sum of bend strain in two orthogonal directions, as well as twist strain and axial strain, which is strain in the longitudinal direction of the fiber sensor. From these four position-dependent quantities, the shape of the fiber sensor can be reconstructed. A detailed description of the shape sensing technology is provided in documents U.S. Pat. No. 8,773,650 B1 and U.S. Pat. No. 9,784,569 B1. For high-accuracy shape sensing, accurate fiber sensor properties are needed in the shape reconstruction model. These properties can be determined for each individual fiber sensor in a calibration process.

An OSS fiber sensor inserted in a lumen of a medical device may experience a varying radius of curvature. The medical device may be pre-shaped and during handling of the device it will change its form. The smallest radius of curvature encountered by the fiber sensor depends on the design of the device, the fiber sensor itself and the environment that it is being used in. The vasculature of a human can, for example, be very tortuous. To be able to access these kind of vessels, more flexible devices will be used. Further, during handling it is possible that the medical device will kink, i.e. will experience a localized very sharp bend. Therefore, an OSS fiber sensor inside these devices should be able to withstand small radii of curvature. In the limit of radius of curvature to zero, the fiber sensor will simply break. However, the optical shape sensing technology gives another limit, which is related to the minimum measurable bend radius of the fiber sensor.

The minimum measurable bend radius of the fiber sensor is proportional to the core distances of the outer cores from the fiber sensor center, and inversely proportional to the scan wavelength range of the light used for interrogating the cores. Thus, in order to reduce the minimum measurable bend radius of the sensor, it seems to be straightforward to increase the scan wavelength range or to reduce the outer core distances. Reducing the outer core distances does not only reduce the sensitivity to bend strain, but also the sensitivity to twist strain, as the sensitivity to twist strain scales with the square of the outer core distance. The required accuracy on the twist is very high, therefore reducing the outer core distance is not favorable. Increasing the scan wavelength range is disadvantageous for other reasons. It decreases the signal-to-noise ratio, because the resonance peak fills the spectrum relatively less. Further, the delay length between two consecutive nodes (data points as a function of position on the fiber sensor) is decreased, giving an increase of data points for the same physical length of the fiber sensor.

SUMMARY OF THE INVENTION

It is an object of the present invention to provide a method of representing shape of an optical fiber sensor, which improves accuracy of the reconstructed shape.

It is a further object of the present invention to provide a method of representing shape of an optical fiber sensor which does not require redundancy of the number of fiber sensor cores of the fiber sensor to achieve high accuracy of shape reconstruction.

It is a further object of the present invention to provide a method of representing shape of an optical fiber sensor which enables representing shapes with a reduced minimum bend radius with high accuracy.

It is a further object of the present invention to provide a corresponding system for representing shape of an optical fiber sensor.

It is still further object of the present invention to provide a computer program enabling a system for representing shape of an optical fiber sensor to carry out the method mentioned above.

According to a first aspect of the invention, a method of representing the shape of an optical fiber sensor having a central core and a plurality of outer cores is provided, each core comprising one or more sensing elements, the method comprising:

(a) optically interrogating the cores of the fiber sensor from an incident optical wave over a wavelength range centered on a resonance wavelength of the one or more sensing elements, wherein the wavelength range is associated with a detection limited to a minimum radius of curvature along the fiber sensor;

(b) reconstructing the shape of the fiber sensor involving processing of interferometric signals received from the optical interrogation of the cores, including reconstructing the shape of at least one out-of-range section along the fiber sensor which is a section having a radius of curvature lower than the minimum radius of curvature, wherein reconstructing the shape of the at least one out-of-range section includes calculating curvature of the fiber sensor in the at least one out-of-range section from interferometric signals received from the interrogation of the central core in the at least one out-of-range section;

(c) displaying the shape of the fiber sensor including the at least one out-of-range section.

The present invention enables representation of the shape of an optical fiber sensor even in sections along the fiber sensor in which the radius of curvature of the fiber sensor is smaller than the minimum measurable bend radius. A section along the fiber sensor in which the radius of curvature is lower than the minimum measurable bend radius is referred to as "out-of-range section" in the present disclosure. To be able to represent the shape of an optical fiber sensor in an out-of-range section, the invention does not require redundancy in the number of outer cores, nor does it require an increased scan wavelength range, nor a decreased outer core distance from the center. In an out-of-range section, one or more of the outer cores of the fiber sensor do not provide interferometric signals upon interrogation as the wavelength shift of the shape sensing element(s) in one or more outer cores exceeds the limits of the scan wavelength range in an out-of-range section. Thus, in an out-of-range section, shape reconstruction cannot be based on measured strain in the outer cores. The invention proposes to derive the strain in an out-of-range section from signals received from the optical interrogation of the center core in the out-of-range section and to calculate curvature from the bend-induced strain in the center core. Calculating curvature of the fiber sensor in the at least one out-of-range section may comprise calculating curvature of the fiber sensor at a plurality of positions along the out-of-range section.

As a preferred embodiment, the invention may be based on the insight that there is a nonlinear effect in the relation between applied stress due to bending and strain. While this nonlinear effect is negligible for small amounts of strain, it is observable for high strain values, as it is the case in an out-of-range section in which the radius of curvature is very small. As a consequence, the signal of the central core provides a measurable contribution of strain owing to curvature from which the radius of curvature (bend radius) may be deduced despite the fact that the resonance wavelengths of one or more of the outer cores are shifted beyond the limits of the scan wavelength range. While in sections with larger bend radii the central core does not observably contribute to strain signals, this is different in an out-of-range section, where the bend radius or radii are very small.

The optical fiber sensor used in the method according to the invention may be a standard optical fiber sensor with three outer cores and one central core. The outer cores may be helically wound around the center core. The sensing elements of the cores may be Fiber Bragg Gratings (FBGs). The number of outer cores and the type of sensing elements may be different than indicated before.

The method according to the invention enables representing shape of an optical fiber sensor with high accuracy, also in one or more out-of-range sections where conventional methods of representing shape fail.

Since the method according to the invention does not require redundancy in the number of fiber sensor cores, costs may also be saved.

Preferred embodiments are described in the dependent claims or are described in the subsequent portions of the description.

In an embodiment, reconstructing the shape of the at least one out-of-range section may further include interpolating one or more quantities in the at least one out-of-range section from one or more quantities of the same type in at least one section adjacent the at least one out-of-range section.

In a section adjacent an out-of-range section, i.e. where the radius of curvature is not below the minimum measurable bend radius, strain measurements can be performed as usual and with high accuracy. From these measurements, one or more quantities of the same type as in the adjacent section(s) may be interpolated, especially linearly interpolated, in the out-of-range section. Phase measurements in two adjacent sections before and after the out-of-range section may be used for the interpolation.

Preferably, the one or more quantities may include one or more quantities varying slowly along the out-of-range section.

These quantities may be any quantity required for shape reconstruction except curvature or bend radius. While the bend radius will be too small in the out-of-range section, the length of this section will also be limited, e.g. when the fiber sensor is bent over an angle that represents not much more than e.g., a U-turn or a kink. Hence, it is fair to assume that in this section most quantities (except curvature) will exhibit a small amount of change. Thus, interpolation of these quantity or quantities, in particular linear interpolation, will be sufficient for accurate shape reconstruction.

The one or more quantities which typically vary slowly in the out-of-range section, may be bend angle (direction of bend), twist angle, and/or common mode strain. Common mode strain is strain common to all cores, and typically includes temperature strain and axial strain.

In an embodiment, step a) may include measuring position-dependent strain through the optical interrogation of the central core in the at least one out-of-range section.

As already mentioned above, there is a non-negligible nonlinear effect between applied stress due to bending and strain when the bend radius is very small. Thus, while the outer cores in view of their comparably large core distance from the fiber sensor center do not provide strain signals useful for shape reconstruction, the central core in contrast provides a measurable contribution of strain owing to curvature. This contribution to strain can be measured and used in the shape reconstruction of the out-of-range section of the optical fiber sensor. In this embodiment, curvature of the optical fiber sensor may be calculated from the derivative of the position-dependent phase differences of the signals from the interferometer received from the center core.

In an embodiment, calculating curvature of the fiber sensor in the at least one out-of-range section may comprise calculating curvature using a nonlinear relationship between strain and curvature.

Preferably, calculating curvature of the fiber sensor in the at least one out-of-range section comprises calculating curvature using a linear relationship between strain and squared curvature, or in other words, a quadratic relationship between strain and curvature.

Using a linear relationship between strain and squared curvature thus makes use of the lowest order of the nonlinear relationship between applied stress and strain, i.e. makes use of the second order of the nonlinear effect. While it would also be possible to use higher orders than the second order of the nonlinear relationship between strain and curvature, using the second-order (quadratic) relationship reduces calculation complexity while achieving high accuracy.

In order to find the proportionality factor between strain and squared curvature, it may be provided in a further embodiment that the proportionality factor is determined prior to interrogating the fiber sensor by calibrating the optical fiber sensor.

Calibrating the optical fiber sensor may comprise bending the fiber sensor in a region of small length along the length of the fiber sensor into a number of different bend radii equal to or larger than the minimum radius of curvature, optically interrogating the cores to obtain interferometric signals from the cores from a plurality of positions along the fiber sensor, calculating common mode strain and curvature from the interferometric signals along the fiber sensor, and calculating the proportionality factor from the common mode strain and squared curvature.

In this way, the proportionality factor can be determined with high accuracy.

When position dependent curvature in an out-of-range section is known from the distributed strain measurement of the center core in the out-of-range section, the position dependent derivative of the phase difference (strain) of the outer cores can be calculated in the out-of-range section using that known position dependent curvature.

In a further embodiment, step b) may further comprise identifying at least one of start and end of the at least one out-of-range section.

Identifying start and/or end of the at least one out-of-range section further improves the method according to the invention as the steps of interpolation of one or more quantities in the at least one out-of-range section and/or using the strain measurement from the center core based on a nonlinear effect between applied stress and strain may be started and/or finished at the right positions along the fiber sensor, while in not-out-of-range sections shape measurement and reconstruction can be performed with high accuracy as usual.

The step of identifying may comprise setting at least one of a threshold of curvature, a threshold of absolute value of phase difference between two successive sample points in the signals received from the interrogation.

This embodiment makes use of the notion that in the part of the fiber sensor shortly before the out-of-range section, the curvature will increase and start to approach the maximum attainable value. Also, the absolute value of the difference in phase between two successive sample points starts to increase in the same part of the fiber sensor to $\pi$ rad. Similar notions hold for the part of the fiber sensor beyond the out-of-range section. In the present embodiment, the threshold may be advantageously set for both the curvature and the phase difference to mark the position of the start and/or end of the out-of-range section.

The step of identifying start of the at least one out-of-range section may comprise identifying when at least one of curvature and absolute value of phase difference increases and starts to approach the at least one of the threshold curvature, the threshold of absolute value of phase difference. The step of identifying end of the at least one out-of-range section may comprise identifying when at least one of curvature and absolute value of phase difference decreases and starts to fall below the at least one of the threshold of curvature, the threshold of absolute value of phase difference.

According to a second aspect, a system for representing shape of an optical fiber sensor having a central core and a plurality of outer cores, each core comprising one or more sensing elements, is provided, comprising:

(a) an interrogation module configured to optically interrogate the cores of the fiber sensor from an incident optical wave over a wavelength range centered on a resonance wavelength of the one or more sensing elements, wherein the wavelength range is associated with a detection limited to a minimum radius of curvature along the fiber sensor;

(b) a reconstruction module configured to reconstruct the shape of the fiber sensor involving processing of interferometric signals received from the optical interrogation of the cores, including to reconstruct the shape of at least one out-of-range-section along the fiber sensor which is a section having a radius of curvature lower than the minimum radius of curvature, wherein the reconstruction module is configured to reconstruct the shape of the at least one out-of-range-section from calculating curvature of the fiber sensor (12) in the at least one out-of-range section from interferometric signals received from the interrogation of the central core (16) in the at least one out-of-range section;

(c) a display unit configured to display the shape of the fiber sensor including the at least one out-of-range section.

It shall be understood that the claimed system may have similar and/or identical preferred embodiments as the claimed method, in particular as defined in the dependent claims and as disclosed herein.

According to a third aspect of the present invention, a computer program comprising program code means for causing the system according to the second aspect to carry out the steps of the method according to the first aspect is provided, when said computer program is carried out on the system.

BRIEF DESCRIPTION OF THE DRAWINGS

These and other aspects of the invention will be apparent from and elucidated with reference to embodiment(s) described hereinafter. In the following drawings.

DETAILED DESCRIPTION OF THE INVENTION

Figure 1:
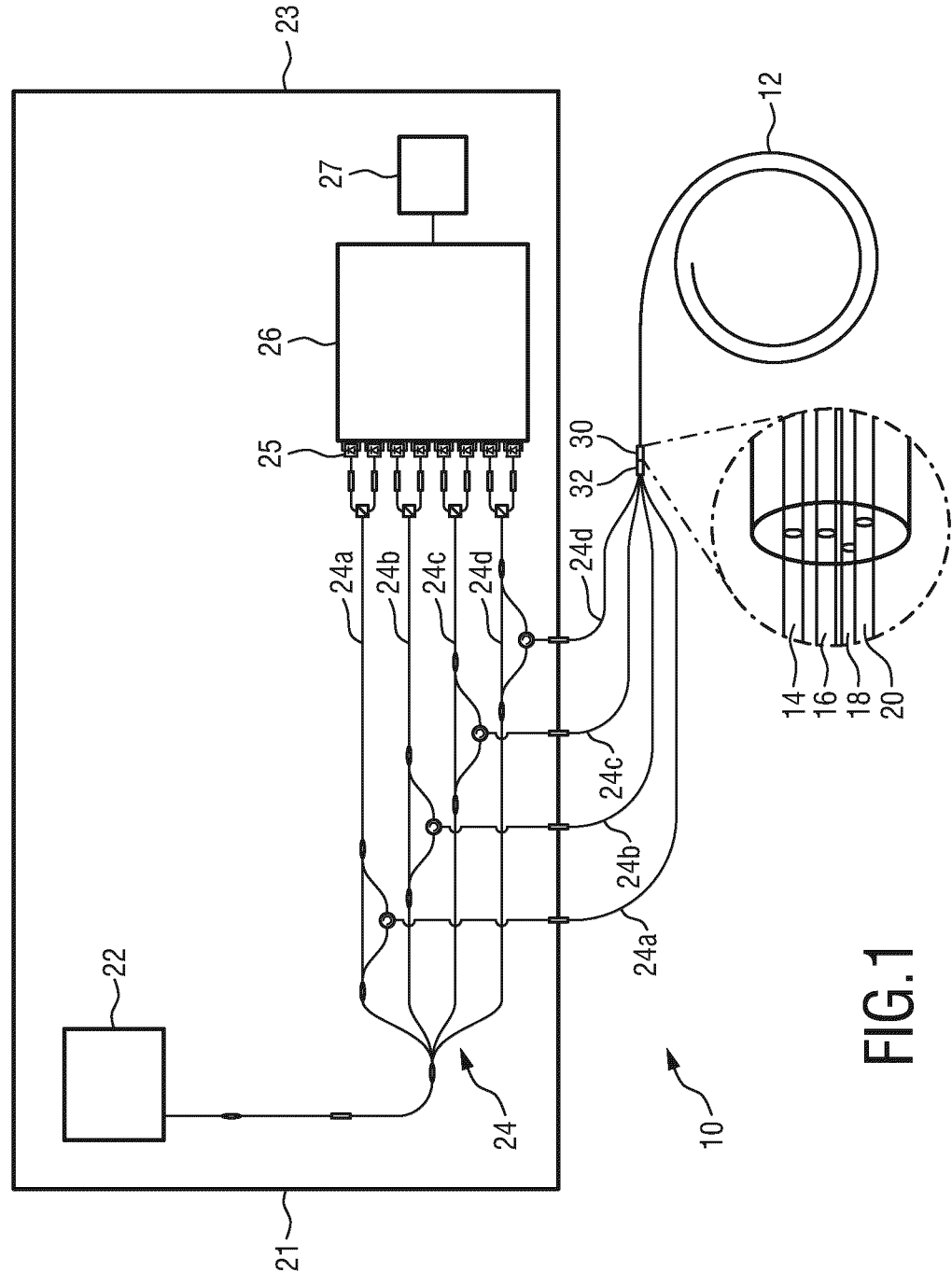
FIG. 1 shows a block diagram illustrating a system for representing shape of an optical fiber sensor.

FIG. 1 schematically shows parts of a system 10 configured for representing shape of an optical fiber sensor 12.

The system 10 may be configured as a multi-channel optical frequency domain reflectometry (OFDR)-based and distributed-strain sensing system for interrogating the fiber sensor 12 and reconstructing shape of the optical fiber sensor 12. The optical fiber sensor may have embedded therein a plurality of fiber cores 14, 16, 18, 20, in the present embodiment four cores with one center core 16 and three outer cores 14, 18, 20. The optical fiber sensor 12 may be a standard fiber sensor as known in the field of optical shape sensing.

Figure 2:
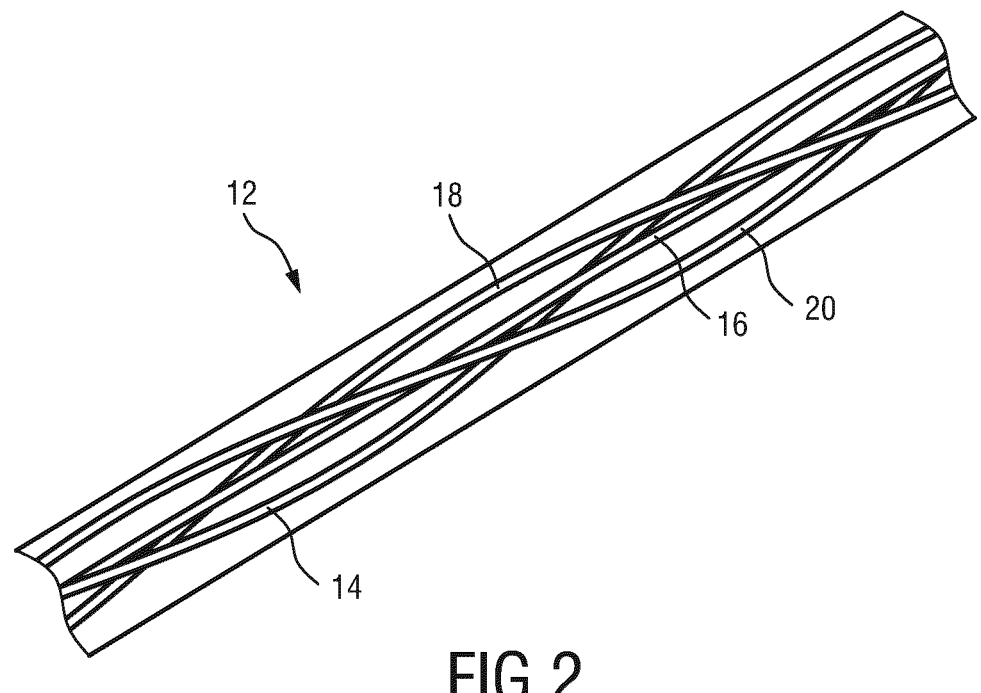
FIG. 2 shows a perspective view of an optical fiber sensor for use in the system of FIG. 1.
Figure 3:
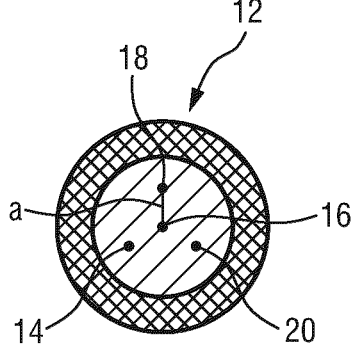
FIG. 3 shows a cross-section of the optical fiber sensor in FIG. 2.

FIG. 2 shows a piece of length of the optical fiber sensor 12 and the cores 14, 16, 18, 20. FIG. 3 shows a cross-section of the optical fiber sensor 12 in a plane perpendicular to the longitudinal center axis of the optical sensor 12. The outer cores 14, 18, 20 are spiraled around the center core 16. The center core 16 is arranged on the center axis of the optical fiber sensor 12. The outer cores 14, 18, 20 are angularly spaced with respect to one another in azimuthal direction around the longitudinal center axis of the optical fiber sensor 12. The longitudinal center axis coincides with the center core 16. According to a number of four cores in the present embodiment, the angular spacing between neighboring outer cores may be 120°. In FIG. 3, a denotes the distance of an outer core from the center. The distance a may be the same for all outer cores 14, 18, 20, but may also be different.

With reference again to FIG. 1, the system 10 comprises an interrogation unit 21 and a reconstruction unit 23. The interrogation unit 21 and the reconstruction unit may be integrated as one apparatus as shown in FIG. 1. The interrogation unit 21 may comprise a tunable light source 22 which can be swept through a range of optical frequencies, also referred to as scan wavelength range. The light emitted by the light source 22 is coupled into an optical interferometric network 24 having optical channels 24a, 24b, 24c, 24d according to the number of fiber cores 14, 16, 18, 20 of the optical fiber sensor 12. In case the optical fiber sensor 12 has less or more than four cores, the optical interferometric network 24 may have a corresponding lower or larger number of optical channels.

When the tunable light source 22 is swept through a range of optical frequencies, each channel 24a, 24b, 24c, 24d and thus each fiber core 14, 16, 18, 20 of the optical fiber sensor 12 is simultaneously and independently optically interrogated, and the interferometric signals based on the reflection spectrum returning from each of the fiber cores 14, 16, 18, 20 are routed to a processing unit or data acquisition unit 26 via respective photodetectors 25. The processing unit may further reconstruct the 3D-shape of the fiber sensor 12 from the distributed strain measurements from the cores 14, 16, 18, 20. The reconstructed shape may be visually displayed on a display unit 27. The system 10 is especially configured to carry out the method according to the present disclosure.

In an embodiment of the optical fiber sensor 12, the fiber sensor cores 14, 16, 18, 20 may have fiber sensor Bragg gratings (FBGs) formed by periodic variations in the refractive index. For the sake of simplicity, FBGs having a single resonance wavelength are considered herein. An FBG reflects light of a certain wavelength (resonance wavelength) that depends on the grating period of the FBG, and transmits all other wavelengths. Due to a bend of the optical fiber sensor 12, the grating period is affected by strain, and measurement of the reflected wavelength for any position along the fiber sensor allows determining the local strain of the fiber sensor 12.

In a method of representing shape of the optical fiber sensor 12, the cores 14, 16, 18, 20 of the fiber sensor 12 are optically interrogated from an incident optical wave supplied by the light source 22. Optical interrogation of the optical fiber sensor 12 gives the information needed to, in principle, reconstruct the three-dimensional shape of the whole fiber sensor 12 in real time. Given an appropriate reference strain, it is possible to know the exact orientation and position of the complete fiber sensor 12 in real time.

The responses of the cores to strain and temperature are measured by the system 10 as phase differences of the optical signals from the interferometric network 24, as a function of delay (position) along the optical fiber sensor 12. The phase differences are obtained with respect to a reference measurement in which the optical fiber sensor lies in a well-defined shape, for example a completely straight shape. From the phase differences of the cores 14, 16, 18, 20 relative to the reference measurement, the strain and temperature differences can be deduced for each core. The strain signals will be the sum of bend strain in two orthogonal directions, as well as twist strain and axial strain, which is strain in the longitudinal direction of the fiber sensor 12. From these four position-dependent quantities, the shape of the optical fiber sensor 12 can be reconstructed.

Thus, the shape of the optical fiber sensor 12 may be calculated from the position-dependent strain signals measured for the several cores 14, 16, 18, 20 inside the fiber sensor 12. For example, bending the fiber sensor 12 in a plane defined by an outer core and the center of the fiber sensor 12 will result in a strain on that core if that core is arranged in a distance from the center of the fiber sensor 12:

$$\varepsilon = \frac{a}{r} \tag{1}$$

where ε is the strain experienced by the core at distance a from the fiber sensor center, due to a bend with a radius of r. The bend strain is measured here relative to the straight and unstrained situation of the fiber sensor 12. The magnitude of the strain can be deduced from the amount of spectral shift of the reflected light received from the cores of the fiber sensor 12. In case the fiber sensor 12 contains FBGs as sensing elements, and due to the periodic nature of the FBGs, this fiber sensor 12 will reflect the light of one particular wavelength, i.e. the resonance wavelength. In case the fiber sensor core is elongated (positively strained) relative to the reference measurement, the periodicity of the FBGs will increase, resulting in an increase in resonance wavelength. In case of compressive (negative) strain, the periodicity of the FBGs will decrease, giving a decrease in resonance wavelength. The lower the radius of curvature, the larger the shift in resonance wavelength $\delta\lambda$ (in either positive or negative direction, depending on the location of the core in the bend):

$$\delta\lambda = \lambda_0 \xi \varepsilon = \frac{\lambda_0 \xi \alpha}{r} \sin(\vartheta_{twist}(z) + \varphi) \qquad (2)$$

where $\lambda_0$ is the resonance wavelength of the FBGs in the unstrained situation, and $\xi$ is the strain-optic number, e.g. which may be $\approx 0.8$, that accounts for the strain-induced change of refractive index, which affects the relation between Bragg period and wavelength. The sin function in equation (2) describes the varying location of the outer core 14, 18, or 20 as it is helically twisted around the fiber sensor center. z is the position along the length of the fiber sensor 12. $\vartheta_{twist}$ is the cumulative twist angle of the respective core, which is the sum of the intrinsically present twist in the spun fiber sensor and the externally applied twist. For example, for a fiber sensor with 50 turns per meter, $d\vartheta_{twist}/dz=314$ rad/m. $\varphi$ is an offset angle which is related to the orientation of the bend plane and the angle of the core at a reference position. For reasons of clarity, only strain due to bend is assumed in equation (2).

When an optical fiber sensor, like the optical fiber sensor 12, is used, for example in a medical device like a catheter or guidewire, the device will change its form during handling of the device. For example, if the device is a catheter for introducing into the vasculature of a human, which can be very tortuous, the device and, thus, the optical fiber sensor 12 will experience bends along its length which may have radii of curvature which can be very small. However, in optical shape sensing technology, there is a limit which is related to the minimum measurable bend radius of the optical fiber sensor 12. A section along the fiber sensor 12 in which a radius of curvature is lower than the minimum radius of curvature which can be measured by interrogating the outer cores is referred to as an out-of-range section in the present disclosure.

The minimum bend radius $r_{min}$ of the optical fiber sensor that has a resonance still inside the measured spectrum and thus may be measured may be given as:

$$r_{min} = \frac{2\lambda_0 \xi a}{\Delta\lambda} \qquad (3)$$

For example, for a scan range of $\Delta\lambda=17$ nm and $\lambda_0=1545$ nm, $\xi=0.8$, $\alpha=35$ μm of an outer core, the minimum radius of curvature that can be measured will be 5.1 mm. If the fiber sensor 12 is bent to lower radii of curvature, no signal will be measured for an outer core that is in the bend plane for the given scan wavelength range and the given core distance from the center.

Figure 4:
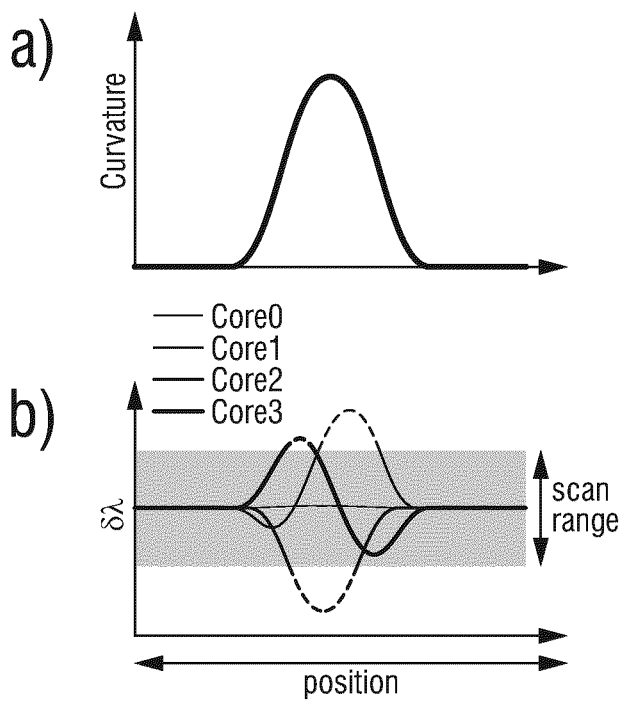
FIG. 4a) shows a graph of an example curvature as function of position along an optical fiber sensor.
FIG. 4b) shows a graph of bend signals for the various cores of the optical fiber sensor for the curvature in FIG. 4a)

FIG. 4 shows an example for a situation where the fiber sensor 12 is bent over a short distance with the radius of curvature too small for detection within the scan wavelength range. FIG. 4a) shows curvature of the optical fiber sensor along the fiber sensor. FIG. 4b) shows corresponding bend signals for the various cores, here denoted as cores 0 to 3, wherein core 0 is the center core and cores 1, 2 and 3 are outer cores. The dotted lines in FIG. 4b) represent the unmeasurable signals beyond the scan wavelength range $\Delta\lambda$, where the wavelength shift $\delta\lambda$ is beyond the scan wavelength range. The scan wavelength range is shown by the grey background in FIG. 4b). As can be taken from FIG. 4b), the sinusoidal behavior of the signals received from the outer cores 1, 2, 3 is only present over a finite range in position owing to the small distance over which the sharp bend extends. Furthermore, the signals are discontinuous when strain is beyond the wavelength range.

From equation (3), it would be straightforward to increase the scan wavelength range $\Delta\lambda$ and/or decrease the distance a of the outer cores from the center. The present disclosure, however, provides an approach different from increasing the scan wavelength range and decreasing the outer core distance from the center to enable high accuracy shape reconstruction of the fiber sensor 12 over the full length, and thus, also in out-of-range sections along the fiber sensor where the radius of curvature of the fiber sensor 12 is lower than the minimum measurable radius of curvature. The method according to the present disclosure also does not require redundancy in the number of outer cores, but works for a standard optical fiber sensor having one center core and three outer cores, for example. It is to be understood that the present disclosure is not limited to the use of a standard optical fiber sensor design.

The method of representing shape of an optical fiber sensor, like optical fiber sensor 12, according to the present disclosure includes reconstructing the shape of an out-of-range section along the fiber sensor based on calculating curvature of the fiber sensor (12), preferably at a plurality of positions along the at least one out-of-range section, from interferometric signals received from the optical interrogation of the center core in the out-of-range section. Shape reconstruction may be further based on one or more quantities obtained from interpolating one or more quantities of the same type from one or two sections adjacent the out-of-range section.

In the following description, using quantities obtained from signals received from the optical interrogation of the center core in the out-of-range section for shape reconstruction of the fiber sensor 12 in an out-of-range section will be described in more detail.

In the relation between applied stress due to bending and strain, a second-order nonlinear effect exists. For small amounts of strain this effect is negligible, but for high-strain values it can be observed well. As a consequence, the signal of the central core provides a measurable contribution of strain owing to curvature from which the bend radius may be deduced despite the fact that the resonance wavelengths of the outer cores, like cores 14, 18, 20, are shifted beyond the scan wavelength range. This may be explained as follows.

For small amounts of stress $\sigma$ (amount of force per unit cross-sectional area), the relation with the ensuing strain $\varepsilon$ (relative elongation), is linear with a proportionality constant E called Young's modulus. For large strains, Young's modulus is dependent on strain as given by the following equation:

$$E = \frac{\sigma}{\varepsilon} = E_0\left(1 + \frac{\gamma}{2}\varepsilon\right) \qquad (4)$$

Figure 5:
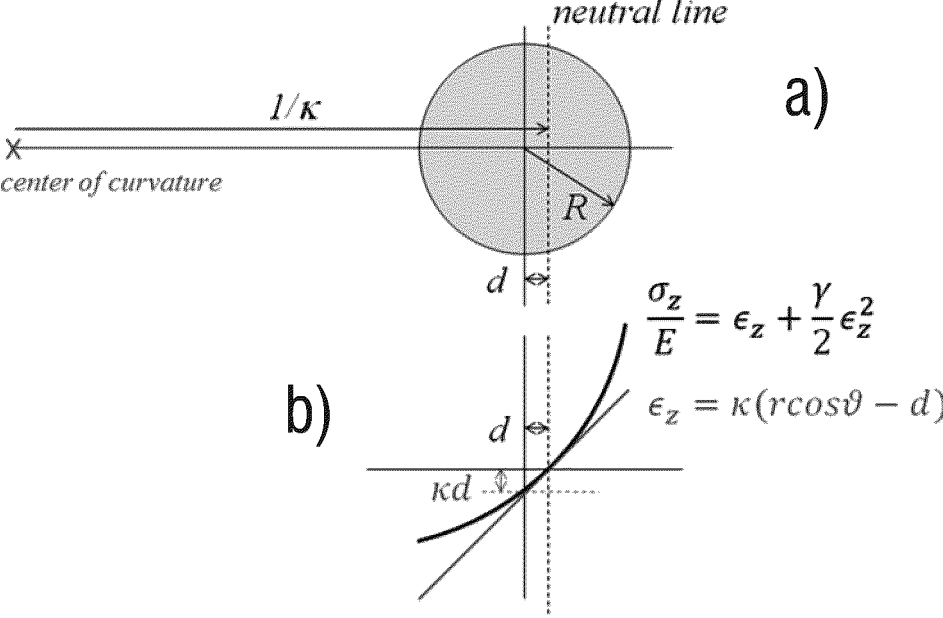
FIG. 5a) shows a cross-section of an optical fiber sensor subject to a curvature.
FIG. 5b) explains the nonlinear relationship between applied stress and strain.

The quantity $E_0$ is Young's modulus for small strain values. The non-linear term $\gamma\varepsilon/2$ describes the strain dependence of Young's modulus and $\gamma$ is a proportionality constant. In steady state, the integral of stress $$\sigma = E_0\left(\varepsilon + \frac{\gamma}{2}\varepsilon^2\right)$$

over the cross-section should always be zero, otherwise the fiber sensor would deform and/or move. For a fiber sensor with a bend and considering only the linear term, the requirement of zero integral stress is fulfilled, when exactly half the cross-section has negative (compressive) strain and the other half positive (tensile) strain. Zero strain is exactly midway of the cross-section. Including the non-linear term shifts the neutral line of zero strain towards the tensile part in order to compensate for the quadratic term that increases the absolute value of the stress in the tensile part and decreases the absolute value of the stress in the compressive part ($\gamma > 0$). A graphical representation of these aspects is given in FIGS. 5$a$) and $b$). The shift d of the neutral line is curvature-dependent:

$$d = \frac{1}{8}\gamma\kappa R^2.$$

The quantity R is the radius of the fiber sensor, and $\kappa$ is the curvature. The strain in the center of the fiber sensor due to bend is not equal to zero and amounts to $$\varepsilon(0) = \kappa d = \frac{1}{8}\gamma\kappa^2 R^2.$$

This means that the central core in the fiber sensor will experience a strain which is quadratically dependent on curvature. This signal can be measured and used to restore the signals of the outer cores in the regions beyond the scan wavelength range, i.e. the out-of-range sections depicted in FIG. 4$b$) as dotted lines. Subsequently, the shape of the fiber sensor 12 can be calculated even in the region of too high curvature, i.e. bend radius below the minimum measurable bend radius.

Figure 6:
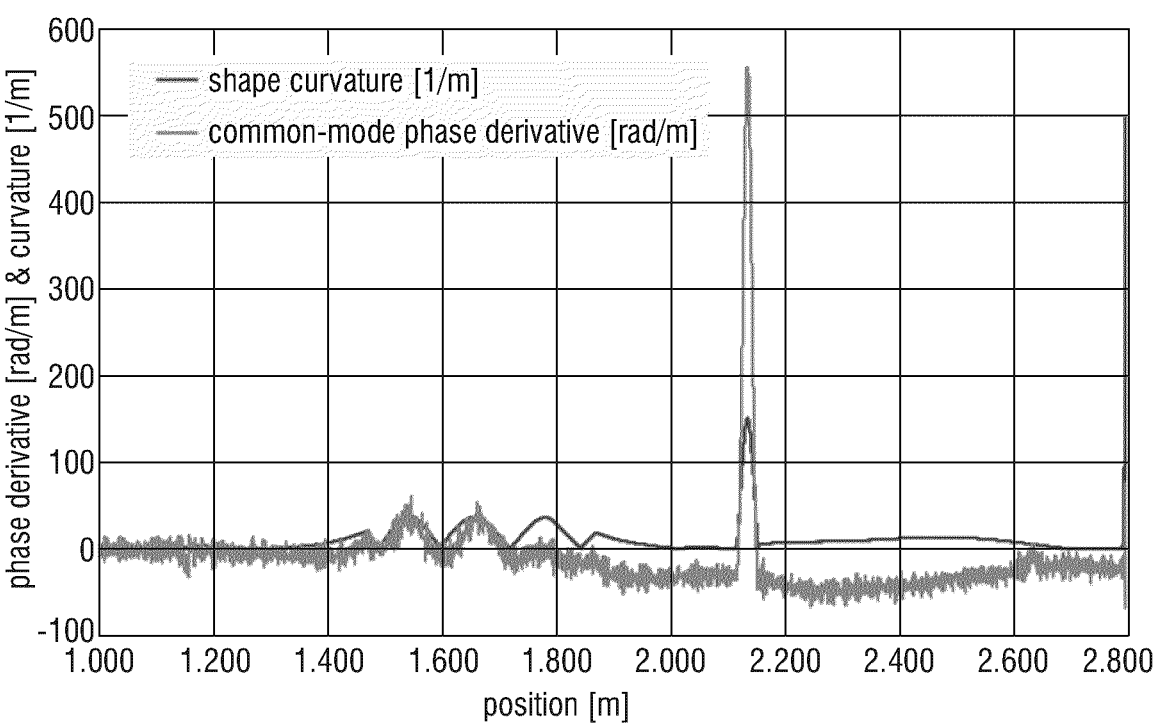
FIG. 6 shows a graph of measured phase derivative and curvature as a function of position along an optical fiber sensor.

The proportionality constant $\beta$ between curvature squared and common mode strain, i.e. the factor $$\frac{1}{8}\gamma R^2$$

needs to be known in order to be able to evaluate curvature from the signal on the central core. The factor $\beta$ may be found by a calibration procedure performed on the optical fiber sensor. The calibration may be performed as follows: The fiber sensor is bent over a small region of interest into various bend radii in such a way that the ensuing signals remain in the wavelength scan range, i.e. also for the outer cores. From the signals of the total of 4 cores, the common mode strain and the curvature are calculated. An example of such a measurement is given in FIG. 6. In FIG. 6, shape curvature and common-mode phase derivative are plotted against position along the fiber sensor. Due to a bend with a small radius, the curvature peaks to 150 m$^{-1}$ around a position of 2.15 m in this example. FIG. 6 shows the common-mode phase derivative from which the common-mode strain may be calculated. The proportionality constant between common-mode strain and phase derivative may be, in a practical example, approximately $-0.106\mu\varepsilon/(\text{rad/m})$.

According to FIG. 6, at a position around 2.15 m, the curvature peaks to 150 m$^{-1}$, and the phase derivative to 550 rad/m in this example.

Figure 7:
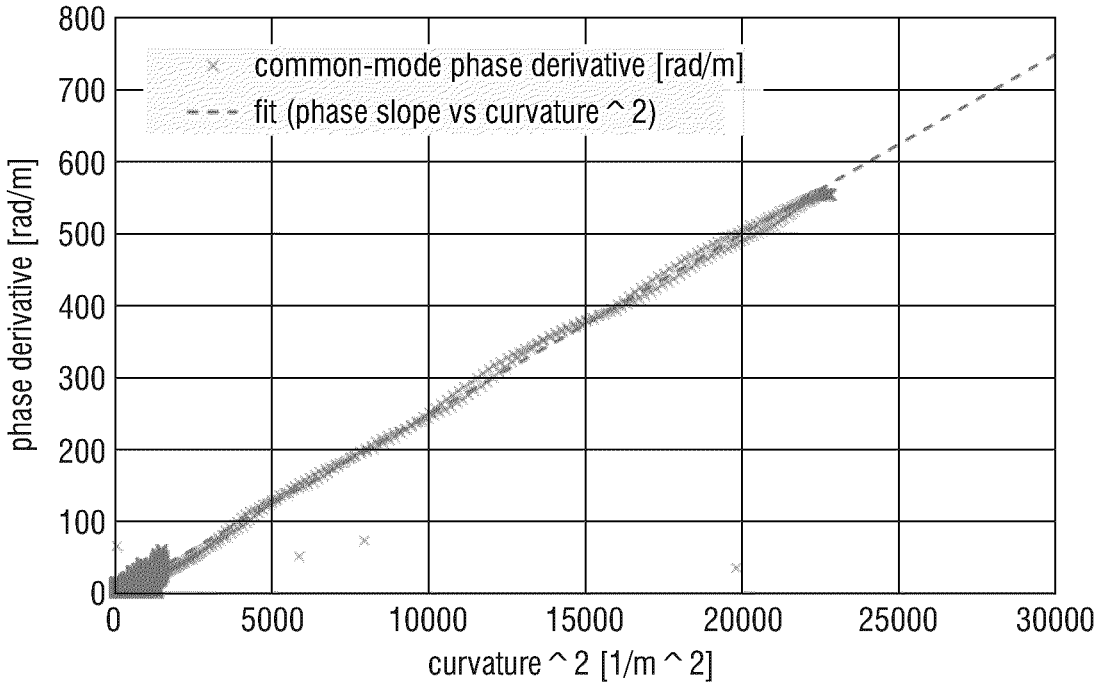
FIG. 7 shows, based on FIG. 6, a graph of phase derivative as a function of squared curvature.

FIG. 7 shows the common-mode strain represented as the phase derivative of the interferometric signal as shown in FIG. 6 versus the square of the curvature as shown in FIG. 6. As can be taken from FIG. 7, the graph is linear with a slope of $\beta = 0.025$ rad×m. This corresponds to a $\gamma$-value for the strain dependency of Young's modulus of 5.4.

When considering not only the bend strain linear in curvature, but also the bend-induced common-mode strain quadratic in curvature, the corresponding phase derivative representative of strain on a fiber sensor core may be written as follows:

$$\frac{d\Delta\varphi}{dz} = \frac{a}{SF}\kappa\sin(\theta_{bend} + \theta_{helix} + \theta_{twist} + \Delta) + \frac{d\Delta\varphi_{common}}{dz} + \beta\kappa^2 \qquad (5)$$

In equation (5), $\Delta\varphi$ is the difference in phase between measurement of an actual shape and reference shape (usually a straight shape) of the fiber sensor; $\alpha$ is the distance of the respective core from the center of the fiber sensor. SF is a constant describing the relation between curvature and phase derivative; $\theta_{bend}$ gives the direction of the bend, $\theta_{helix}$ represents the angle of the helical winding of the outer cores intrinsic in the fiber sensor; $\theta_{twist}$ is the additional angle due to twisting of the fiber sensor by an external torque; and A represents the angular (azimuthal) position of the respective core in the cross-section of the fiber sensor with respect to a reference axis. The second term on the right-hand side of equation (5) represents axial and temperature strain (i.e. common-mode strain), while the last term in equation (5) is the nonlinear bend-induced strain proportional to the square of the curvature. The quantities $\alpha$, SF, $\theta_{helix}$, and $\Delta$ may be determined in a regular calibration procedure applied to each optical fiber sensor under consideration.

For sensors with the same radius R, the proportionality factor $\beta$ (see above) typically will not vary significantly from optical fiber sensor to optical fiber sensor, as the stress/strain non-linearity represents a property of the glass material. For each of the various cores in an optical fiber sensor, for example four cores as shown in FIGS. 2 and 3, an equation such as equation (5) can be written with the notion that the values for $\alpha$ and $\Delta$ will be different for each core as well as the measured phase derivative on the left hand side of equation (5).

Figure 8:
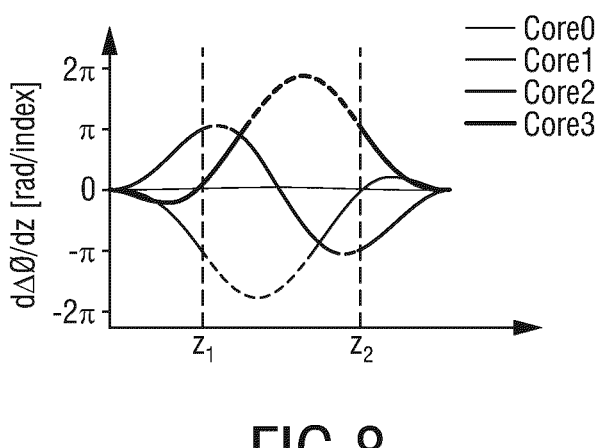
FIG. 8 shows a graph of phase derivatives of various cores of an optical fiber sensor in a region of high curvature.

With reference to FIG. 8, now considering a region $z_1 < z < z_2$ of the fiber sensor with high curvature such that the outer cores, like cores 14, 18, 20, will experience a strain too large for being measurable in the given scan wavelength range. Within the region $z_1 < z < z_2$, the phases of the outer cores need to be restored, as there are no measurable bend signals in this region, as indicated by dotted lines. For the regions $z < z_1$ and $z > z_2$ all information is present in order to reconstruct shape from the measurement of distributed strain (phase derivative) of the outer cores, i.e. the bend angle $\theta_{bend}$, the twist angle $\theta_{twist}$ and curvature $\kappa$ are known as a function of distance along the fiber sensor as well as the common-mode effects due to axial strain and temperature, $$\frac{d\Delta\varphi_{common}}{dz}.$$

The method of representing shape according to the present disclosure may also make use, when reconstructing the shape of the fiber sensor in an out-of-range section, of one or more quantities obtained from interpolating one or more quantities of the same type from one or two sections adjacent the out-of-range section. In the present example, the out-of-range section is the region between $z_1$ and $z_2$. In the region of interpolation, the bend radius will be small and, consequently, the length of interpolation will also be limited when the fiber sensor is bent over an angle that represents not much more than, e.g., a U-turn or a kink. Hence, it is justified to assume that in this region most quantities (except curvature) will exhibit a small amount of change, thus are only slowly varying. Thus, the method according to the present disclosure proposes to interpolate, especially linearly interpolate, bend angle $\theta_{bend}$, twist angle $\theta_{twist}$, and/or common-mode signals $$\frac{d\Delta\varphi_{common}}{dz}$$

in the region between $z=z_1$ and $z=z_2$ from bend angle $\theta_{bend}$, twist angle $\theta_{twist}$, and/or common-mode signals $$\frac{d\Delta\varphi_{common}}{dz}$$

in the regions before $z_1$ and/or after $z_2$. It is to be noted here that bend angle is not to be mixed up with curvature.

Since the phase derivative in equation (5) can be measured for the central core (core 0 in FIG. 8), all quantities of equation (5) are known, either by measurement, calibration or linear interpolation except the curvature $\kappa$. Thus, equation (5) can be solved for the curvature $\kappa$ at every node in the region $z_1<z<z_2$ for the central core.

For the outer cores (core 1, 2, 3 in FIG. 8), all quantities of equation (5) are now known, except the phase derivative of the left hand side of equation (5). However, since all quantities of the right hand side of equation (5) are known for the outer cores, including curvature which is known from the strain measurement on the center core, the phase derivative of the left hand side of equation (5) can now be calculated for each outer core in the region $z_1<z<z_2$ using the quantities of the right hand side obtained from the previous steps. If necessary, an offset may be added so that the phase and its derivative are sufficiently continuous.

As now all the phases of all the cores are known, the standard procedure for shape reconstruction can now be applied in the out-of-range section.

The method according to the present disclosure may also include a step of identifying start and/or end of an out-of-range section. Identification of start and/or end of an out-of-range section may be performed as follows. In the part of the optical fiber sensor prior to an out-of-range section, curvature will increase and start to approach the maximum attainable value. For a typical interrogator, this value may be around 200 m$^{-1}$. Further, the absolute value of the difference in phase between two successive sample points starts to increase in that same part of the optical fiber sensor to $7r$ rad. Similar considerations hold for the part of the optical fiber sensor beyond the region of interest, i.e. at or after the end of the out-of-range section.

A threshold for both the curvature and the phase difference to e.g. 180 m$^{-1}$ and 2.8 rad respectively may be advantageously set to mark the position of the start and end of the out-of-phase region.

Figure 9:
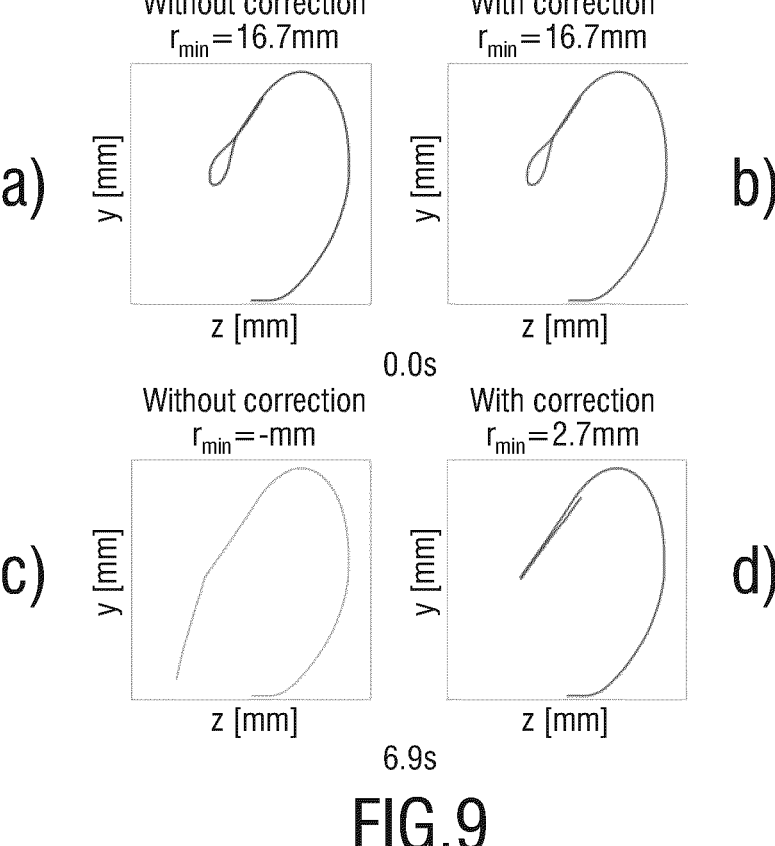
FIG. 9a) shows a graph representing shape of an optical fiber sensor having a loop with a radius of curvature of 16.7 mm, wherein shape reconstruction has been performed with a conventional method.
FIG. 9b) shows a graph representing shape of the optical fiber sensor with the same loop as in FIG. 9a), wherein shape reconstruction has been performed with the method according to the invention.
FIG. 9c) shows a graph representing shape of an optical fiber sensor having a curvature with a radius smaller than the minimum radius measurable by a conventional method.
FIG. 9d) shows a graph representing shape of the optical fiber sensor having the same curvature as in FIG. 9c), while shape reconstruction has been performed with the method according to the invention.

With reference to FIG. 9, experiments will be described which shows the efficiency of the method according to the present disclosure. In a first experiment according to FIG. 9a) and b), an optical fiber sensor was provided, and the tip of the optical fiber sensor was folded back onto the fiber sensor so that a loop was created. The shape of the optical fiber sensor was reconstructed twice, once without and once with the small bend radius correction in the shape reconstruction according to the present disclosure. The small bend radius correction was based on the second-order nonlinear effect in the relation between applied stress to bending and strain as described above. FIGS. 9a) and 9b) show the representations of the shape of the optical fiber sensor having the tip folded back onto the fiber sensor. Since the minimum radius of curvature present in the region of the loop was 16.7 mm, shape representation without small bend radius correction (FIG. 9a)) and with small bend radius correction (FIG. 9b)) according to the present disclosure did not reveal a difference.

In a second experiment, the tip of the optical fiber sensor was folded back onto the fiber sensor with a much sharper curvature than in the first experiment, i.e. with a minimum radius of curvature of 2.7 mm. According to FIG. 9d), the shape of the optical fiber sensor could be accurately reconstructed when using the method according to the present disclosure. When not using the method according to the present disclosure, the actual shape could not be represented correctly, but gave an erroneous result. With the method according to the present disclosure, the shape of the optical fiber sensor having a bend radius as small as 2.7 mm can be represented with high accuracy, which is about a factor of 2 smaller than the minimum measurable radius of curvature without increasing the scan wavelength range and without decreasing the outer core distance from the center, and also without redundancy in the number of outer cores.

A computer program comprises program code means for causing the system 10 to carry out the steps of the method according to the present disclosure, when said computer program is carried out on the system 10. The computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A method of representing a shape of an optical fiber sensor having cores comprising of a central core and a plurality of outer cores, each core comprising one or more sensing elements, comprising:

interrogating the cores of the optical fiber sensor via an incident optical wave having a wavelength range;

processing interferometric signals received from the interrogating of the cores;

calculating an out-of-range curvature of at least one out-of-range section along the fiber sensor, wherein the out-of-range curvature has a radius of curvature lower than a minimum measurable radius of curvature defined by the wavelength range; and reconstructing the shape of the fiber sensor based on at least the processed interferometric signals and the out-of-range curvature.

2. The method of claim 1, wherein the calculating the out-of-range curvature of the at least one out-of-range section comprises:

interpolating a first quantity of the at least one out-of-range section based on one or a plurality of second quantities of at least one adjacent section, wherein the first quantity and the one or a plurality of second quantities are of a same type; and calculating the out-of-range curvature based on at least a relationship between a central core curvature and the first quantity.

3. The method of claim 2, wherein the one or a plurality of second quantities is measured by the processing of the interferometric signals received from the interrogating of the cores.

4. The method of claim 2, wherein the type is one or a combination of bend strain, twist strain, axial strain, temperature, and common mode strain.

5. The method of claim 1, wherein the calculating the out-of-range curvature of the at least one out-of-range section comprises:

interpolating a position dependent first quantity of the at least one out-of-range section based on one or a plurality of third quantities of the center core, wherein the one or a plurality of third quantities are measured by the processing of the interferometric signals, and wherein the first quantity and the one or a plurality of third quantities are of a same type.

6. The method of claim 1, wherein the calculating the out-of-range curvature of the at least one out-of-range section comprises calculating central core curvature using a non-linear relationship between strain and central core curvature.

7. The method of claim 1, wherein the calculating the out-of-range curvature of the at least one out-of-range section comprises calculating central core curvature using a linear relationship between strain and squared central core curvature.

8. The method of claim 7, wherein the method further comprises:

calibrating the fiber sensor to determine a proportionality factor between strain and squared central core curvature prior to the interrogating the fiber sensor.

9. The method of claim 8, wherein the calibrating the optical fiber sensor to determine the proportionality factor comprises:

bending the fiber sensor in a region of small length along the length of the fiber sensor into a number of different bend radii equal to or larger than the minimum radius of curvature;

interrogating the fiber sensor to obtain, from the cores, a plurality of interferometric signals of a plurality of positions along the fiber sensor;

calculating common mode strain and curvature from the plurality of interferometric signals along the fiber sensor; and calculating the proportionality factor from the common mode strain and squared curvature.

10. The method of claim 1, wherein the method further comprises:

identifying at least one of a start and an end of the at least one out-of-range section along the fiber sensor.

11. The method of claim 10, wherein the identifying the at least one of the start and the end comprises:

setting at least one of a threshold of curvature and a threshold of absolute value of phase difference between two successive sample points in the signals received from the interrogation.

12. The method of claim 11, wherein the identifying the start of the at least one out-of-range section comprises identifying when at least one of curvature and absolute value of phase difference increases and starts to approach the at least one of the threshold of curvature, the threshold of absolute value of phase difference.

13. The method of claim 11, wherein the identifying the end of the at least one out-of-range section comprises identifying when at least one of curvature and absolute value of phase difference decreases and starts to fall below the at least one of the threshold of curvature, the threshold of absolute value of phase difference.

14. A system for representing a shape of an optical fiber sensor having cores comprising of a central core and a plurality of outer cores, each core comprising one or more sensing elements, comprising:

an interrogation processor configured to interrogate the cores of the optical fiber sensor via an incident optical wave having a wavelength range;

a processor configured to process interferometric signals received from the interrogating of the cores;

a reconstruction processor configured to:

calculate an out-of-range curvature of at least one out-of-range section along the fiber sensor, wherein the out-of-range curvature has a radius of curvature lower than a minimum radius of curvature measurable within the wavelength range; and reconstruct the shape of the fiber sensor based on at least the processed interferometric signals and the out-of-range curvature.

15. A non-transitory computer-readable storage medium having stored a computer program comprising instructions for representing a shape of an optical fiber sensor having cores comprising of a central core and a plurality of outer cores, each core comprising one or more sensing elements, which, when executed by the processor, cause the processor to:

interrogate the cores of the optical fiber sensor via an incident optical wave having a wavelength range;

process interferometric signals received from the interrogating of the cores;

calculate an out-of-range curvature of at least one out-of-range section along the fiber sensor, wherein the out-of-range curvature has a radius of curvature lower than a minimum radius of curvature measurable within the wavelength range; and reconstruct the shape of the fiber sensor based on at least the processed interferometric signals and the out-of-range curvature.

* * * * *